(12) United States Patent
Ikehara et al.

(10) Patent No.: US 7,166,311 B2
(45) Date of Patent: Jan. 23, 2007

(54) PROCESS FOR PRODUCING FAT COMPOSITION CONTAINING HYDROPHOBIC COMPONENTS OF GLYCYRRHIZA

(75) Inventors: Toshinori Ikehara, Hyogo (JP); Mikio Kitahara, Hyogo (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 10/508,903

(22) PCT Filed: Apr. 4, 2003

(86) PCT No.: PCT/JP03/04312

§ 371 (c)(1),
(2), (4) Date: Sep. 23, 2004

(87) PCT Pub. No.: WO03/084556

PCT Pub. Date: Oct. 16, 2003

(65) Prior Publication Data

US 2005/0118289 A1  Jun. 2, 2005

(30) Foreign Application Priority Data

Apr. 4, 2002 (JP) ............................. 2002-102629

(51) Int. Cl.
*A61K 36/48* (2006.01)
(52) U.S. Cl. ................................... 424/757
(58) Field of Classification Search .................... None
See application file for complete search history.

(56) References Cited

U.S. PATENT DOCUMENTS

2004/0028751 A1*  2/2004  Mae et al. .................. 424/684

FOREIGN PATENT DOCUMENTS

| JP | 62-223291 A | 10/1987 |
| JP | 2-134324 A | 5/1990 |
| JP | 02-204417 A | 8/1990 |
| JP | 4-164021 A | 6/1992 |
| JP | 10-130161 A | 5/1998 |
| JP | 2000-191498 A | 7/2000 |
| JP | 2000-204370 A | 7/2000 |
| JP | 2000-239176 A | 9/2000 |
| JP | 2001-103932 A | 4/2001 |
| WO | WO 02/47699 A1 | 6/2002 |

OTHER PUBLICATIONS

Aida, Kaoru et al., "Isoliquiritigenin: A New Aldose Reductase Inhibitor from Glycyrrhizae Radix," *Planta Med.*, 1990, vol. 56, No. 3, pp. 254-258.
Gordon, Michael H. et al., "Antioxidant Activity of Flavonoids Isolated from Licorice," *J. Agric. Food Chem.*, 1995, vol. 43, No. 7, pp. 1784-1788.
Hatano, Tsutomu et al., "Phenolic Constituents of Licorice. II. Structures of Licopyranocoumarin, Licoarylcoumarin and Glisoflavone, and Inhibitory Effects of Licorice Phenolics on Xanthine Oxidase," *Chem. Pharm. Bull.*, 1989, vol. 37, No. 11, pp. 3005-3009.
Tanaka, Yasuo et al., "Antibacterial Compounds of Licorice Against Upper Airway Respiratory Tract Pathogens," *J. Nutr. Sci. Vitaminol*, 2001, vol. 47, No. 3, pp. 270-273.
International Search Report From Corresponding International Application No. PCT/JP03/04312, Dated Jun. 24, 2003, 2 pages.
Patent Cooperation Treaty International Preliminary Examination Report (PCT Article 36 and Rule 70), From Corresponding International Application No. PCT/JP2003/004312, Dated Feb. 17, 2004, 5 pages.
Niu, Guo-guang et al., "Isolation and Purification of Glycyrrhizic Acid With Solvent Extraction," *Separation and Purification Technology*, vol. 44, 2005, pp. 189-196.
Supplementary European Search Report from Application No. EP 03 74 5912, Jul. 29, 2005, 3 pages.

* cited by examiner

*Primary Examiner*—Christopher R. Tate
(74) *Attorney, Agent, or Firm*—Brinks Hofer Gilson & Lione

(57) ABSTRACT

In the present invention, an oil and fat composition containing 10% by weight or more of a specific fat-soluble polyhydric fatty acid ester, in particular, a glycerol fatty acid ester, is used as a solvent for extracting hydrophobic components from licorice. Consequently, it is possible to reduce the production costs for hydrophobic components of licorice which have excellent effects as food and drink, such as health food and food with health claims (food for specified health uses and food with nutrient function claims), pharmaceutical products, etc. It is also possible to improve the stability and handling properties of the resulting composition.

15 Claims, No Drawings

PROCESS FOR PRODUCING FAT COMPOSITION CONTAINING HYDROPHOBIC COMPONENTS OF GLYCYRRHIZA

RELATED APPLICATIONS

This application is a nationalization of PCT application No. PCT/JP03/04312 filed on Apr. 4, 2003, claiming priority to Japanese Application No. 2002-102629 filed on Apr. 4, 2002.

TECHNICAL FIELD

The present invention relates to a process for producing an oil and fat composition containing hydrophobic components of glycyrrhiza (licorice) and being suitable for use in preparing food and drink, such as health food and food with health claims (food for specified health uses and food with nutrient function claims), pharmaceutical products, etc.

BACKGROUND ART

Licorice and a water extract thereof have been used as galenicals having analgesic and antispasmodic actions and an expectorant action, or in food applications. Since glycyrrhizin (glycyrrhizinic acid), which is a main component of licorice, is about 200 times sweeter than sucrose, it is also used as a sweetening agent.

It has also been confirmed that hydrophobic components extracted from licorice or a water-extracted residue of licorice with an organic solvent, such as ethanol, acetone, or ethyl acetate, have many useful effects, such as an antioxidant effect, an antibacterial effect, an enzyme inhibitory effect, an antitumor effect, an antiallergic effect, and an antiviral effect. Furthermore, recent research has found that the hydrophobic components of licorice have a hypoglycemic action and a lipid metabolism-improving action (WO02/47699).

In order to extract such hydrophobic components from licorice, organic solvents are exclusively used. For example, each of Japanese Unexamined Patent Application Publications Nos. 1-149706 and 3-109314 discloses an example of extraction with a hydrophobic organic solvent; Japanese Unexamined Patent Application Publication No. 2-204495 discloses an example of extraction with a mixed solvent of a hydrophobic organic solvent and a small amount of water-soluble organic solvent; Japanese Unexamined Patent Application Publication No. 7-53393 discloses an example of extraction with water and/or a water-soluble organic solvent (preferably, hot water); and Japanese Unexamined Patent Application Publication No. 1-157909 discloses an example of extraction with one of a wide variety of water-soluble organic solvents and hydrophobic organic solvents.

However, the resulting hydrophobic components of licorice do not substantially dissolve in water and common oil, and the extract obtained with such an organic solvent easily cakes and colors, thus being unstable. Therefore, the extract must be formulated so as to be easy to handle and stable. In any of the methods described above, the organic solvent used for extraction results in many unsolved problems, for example, a high production cost and a significant adverse effect on the environment.

SUMMARY OF THE INVENTION

As described above, hydrophobic components of licorice are highly effective in preparing food and drink, such as health food and food with health claims (food for specified health uses and food with nutrient function claims), pharmaceutical products, etc. However, the production cost therefor is high because of the extraction process using an organic solvent only, and the extract is difficult to handle, resulting in difficulty in utilization. Accordingly, it is an object of the present invention to inexpensively obtain hydrophobic components of licorice which are suitable for use in preparing food and which are stable and easy to handle.

The present inventors have conducted intensive research and have found that the object described above can be achieved by using a specific fat-soluble polyhydric alcohol fatty acid ester as a solvent and have also found that an oil and fat composition which can be used in all applications of usual edible oils and fats can be produced. The present invention has been completed based upon these findings.

That is, in a first aspect, the present invention relates to a process for producing an oil and fat composition containing hydrophobic components of licorice, including mixing licorice with an oil and fat solvent containing 10% by weight or more of a fat-soluble polyhydric alcohol fatty acid ester.

Preferably, the process for producing the oil and fat composition containing hydrophobic components of licorice according to the present invention further includes using at least one organic solvent selected from the group consisting of ethanol, acetone, and ethyl acetate. Preferably, the process for producing the oil and fat composition containing hydrophobic components of licorice includes the steps of mixing at least one organic solvent selected from the group consisting of ethanol, acetone, and ethyl acetate with licorice, and then mixing the oil and fat solvent containing 10% by weight or more of the fat-soluble polyhydric alcohol fatty acid ester therewith. In the process for producing the oil and fat composition containing hydrophobic components of licorice, preferably, the oil and fat solvent is composed of only the fat-soluble polyhydric alcohol fatty acid ester. In the process for producing the oil and fat composition containing hydrophobic components of licorice, preferably, the fat-soluble polyhydric alcohol fatty acid ester is a glycerol fatty acid ester. In the process for producing the oil and fat composition containing hydrophobic components of licorice, preferably, the glycerol fatty acid ester is a monoglyceride and/or a diglyceride. In the process for producing the oil and fat composition containing hydrophobic components of licorice, preferably, the glycerol fatty acid ester is a medium-chain triglyceride. In the process for producing the oil and fat composition containing hydrophobic components of licorice, preferably, the glycerol fatty acid ester is a polyglycerol fatty acid ester. In the process for producing the oil and fat composition containing hydrophobic components of licorice, preferably, the polyglycerol fatty acid ester is a polyglycerol condensed ricinoleic acid ester.

In a second aspect, the present invention relates to an oil and fat composition containing hydrophobic components of licorice obtained by any one of the production processes described above.

In a third aspect, the present invention relates to an oil and fat-containing food including the oil and fat composition containing the hydrophobic components of licorice described above.

DETAILED DISCLOSURE OF THE INVENTION

The present invention will be described in detail below.

According to the present invention, a process for producing an oil and fat composition containing hydrophobic components of licorice includes mixing an oil and fat solvent containing 10% by weight or more of a fat-soluble polyhydric alcohol fatty acid ester with licorice.

First, examples of licorice which may be used in the present invention include leguminous plants of the genus *Glycyrrhiza*, such as *Glycyrrhiza uralensis* (*G. uralensis*), *Glycyrrhiza inflata* (*G. inflata*), *Glycyrrhiza glabra* (*G. glabra*), *Glycyrrhiza eurycarpa* (*G. eurycarpa*), and *Glycyrrhiza aspera* (*G. aspera*). Preferred examples include *G. uralensis, G. inflata*, and *G. glabra*. Licorice has long been eaten as food and has also been used as a food additive or a galenical.

Examples of the form of licorice used in the present invention include licorice itself, licorice powder, a water-extracted residue obtained by removing hydrophilic components by extraction with water or the like from licorice or licorice powder, and a dried product of the water-extracted residue. However, an extract obtained by a method in which licorice is subjected to extraction with a common organic solvent (e.g., ethanol, acetone, or ethyl acetate) and the organic solvent is then removed is not considered as the form of licorice used in the present invention.

Next, the solvent used in the present invention is an oil and fat solvent containing 10% by weight or more of a fat-soluble polyhydric alcohol fatty acid ester. If the content of the fat-soluble polyhydric alcohol fatty acid ester is 10% by weight or more, the effect of extracting hydrophobic components from licorice is satisfactorily exhibited.

Any fat-soluble polyhydric alcohol fatty acid ester having at least two hydroxyl groups per molecule can be used in the present invention. Examples thereof include fatty acid esters of glycerol, polyglycerol, sugars, sugar alcohols, and polysorbates. Above all, in view of the high effect of extracting hydrophobic components from licorice, preferred are fat-soluble polyhydric alcohol fatty acid esters having a HLB of 7.0 or less and polyglycerol condensed ricinoleic acid esters which are fat-soluble even with a HLB of more than 7.0. These may be used alone or in combination.

Additionally, the HLB can be determined by the following expression (Kagaku Jiten, first edition, Tokyo Kagaku Dozin Co., Ltd., published on Oct. 1, 1994):

$$HLB = 20 \times (1 - S/A),$$

where S is the saponification number of the ester and A is the acid number of the fatty acid.

As the glycerol fatty acid ester, any ester of glycerol or polyglycerol and the fatty acid which will be described below can be used without limitation. Preferred are glycerol fatty acid esters having a HLB of 7.0 or less and polyglycerol condensed ricinoleic acid esters which are fat-soluble even with a HLB of more than 7.0. In view of the high effect of extracting hydrophobic components from licorice, preferred are monoglycerides and diglycerides. In the case of triglycerides, medium-chain triglycerides are preferable. Polyglycerol fatty acid esters are also preferable. As the polyglycerol fatty acid ester, a polyglycerol condensed ricinoleic acid ester is more preferable. Furthermore, compound lipids, such as phospholipids, may be used. Monoglycerides, diglycerides, and compound lipids, such as phospholipids, are contained as accessory constituents in natural oils and fats and widely used in the food field.

Examples of fatty acid residues constituting the esters described above include those having 4 to 24 carbon atoms. Among them, examples of medium-chain fatty acid residues include those having 8 to 10 carbon atoms. Saturated fatty acids and unsaturated fatty acids thereof may be selected depending on application. For example, when flowability is required, unsaturated fatty acids are preferred. When plasticity is required, saturated fatty acids may be contained. Branched-chain fatty acids, such as isostearic acid, may also be used.

Examples of the saturated fatty acids include caproic acid, caprylic acid, capric acid, lauric acid, myristic acid, palmitic acid, stearic acid, and behenic acid. Examples of the unsaturated fatty acids include oleic acid, linoleic acid, linolenic acid, and ricinoleic acid. Furthermore, ricinoleic acid may form a condensed acid.

In addition to the fat-soluble polyhydric alcohol fatty acid ester, animal and vegetable oils and fats may also be incorporated into the oil and fat solvent used in the present invention. Examples of the animal and vegetable oils and fats include vegetable oils, such as corn oil, rapeseed oil, rapeseed oil with a high erucic acid content, soybean oil, olive oil, safflower oil, cottonseed oil, sunflower oil, rice bran oil, palm oil, and palm kernel oil; animal oils, such as fish oil, beef tallow, lard, milk fat, and yolk oil; oils and fats produced by fractionation, hydrogenation, transesterification, or the like using these oils as starting materials; and mixtures of these oils and fats.

The content of the fat-soluble polyhydric alcohol fatty acid ester in the oil and fat solvent must be 10% by weight or more, as described above. The content of the fat-soluble polyhydric alcohol fatty acid ester in the oil and fat solvent is preferably 20% by weight or more, more preferably 30% by weight or more, still more preferably 50% by weight or more, and particularly preferably 100% by weight.

In the process for producing the oil and fat composition containing hydrophobic components of licorice according to the present invention, the oil and fat solvent is mixed with licorice. Specifically, for example, after the licorice in the above described form and the oil and fat solvent containing the fat-soluble polyhydric alcohol fatty acid ester are stirred, insolubles may be removed by centrifugation, filtration under reduced pressure, pressure filtration, filter pressing, or the like.

In order to improve extraction efficiency, stirring is preferably performed under heating preferably at 30° C. to 100° C., and more preferably at 40° C. to 90° C. In order to prevent degradation due to heating, more preferably stirring is performed under reduced pressure or under nitrogen flow. The stirring time is preferably 1 hour or more, more preferably 1 to 5 hours, and most preferably 1 to 3 hours, although not particularly limited thereto.

Furthermore, from the standpoint of improving the extraction efficiency, the oil and fat solvent is preferably used together with an organic solvent, such as ethanol, acetone, or ethyl acetate, which is commonly used for extraction of hydrophobic components of licorice, and particularly preferably ethanol. In such a case, the amount of the organic solvent used can be decreased compared with the conventional process. Furthermore, an edible oil and fat composition containing hydrophobic components of licorice can also be obtained merely by removing the organic solvent by distillation. Thereby, it is possible to reduce costs by simplifying the production process.

Specifically, licorice may be mixed with a mixed solvent including the oil and fat solvent containing 10% by weight or more of the fat-soluble polyhydric alcohol fatty acid ester and at least one organic solvent selected from the group consisting of ethanol, acetone, and ethyl acetate. Alternatively, at least one organic solvent selected from the group consisting of ethanol, acetone, and ethyl acetate may be mixed with licorice, and then the oil and fat solvent containing 10% by weight or more of the fat-soluble polyhydric alcohol fatty acid ester may be mixed therewith.

In either case, by removing the organic solvent after the stirring step, an oil and fat composition containing hydrophobic components of licorice can be obtained. Additionally, when the oil and fat solvent is mixed after the organic solvent is mixed with licorice, the organic solvent is removed by distillation after mixing the oil and fat solvent and subsequent stirring, not before mixing the oil and fat solvent. If the organic solvent is removed by distillation before the oil and fat solvent is mixed, it becomes difficult to dissolve the residue in the oil and fat solvent, and as a result, a large amount of solvent must be used, the stirring temperature must be increased, or the stirring time must be extended.

In the production method of the present invention, the amounts of licorice, the oil and fat solvent, and the organic solvent used are not particularly limited. When the oil and fat solvent alone is used as the solvent, the amount of the oil and fat solvent is preferably 50 parts by weight or more and more preferably 100 to 500 parts by weight to 100 parts by weight of licorice.

When both the oil and fat solvent and the organic solvent are used, the amount of the oil and fat solvent is preferably 10 parts by weight or more and more preferably 10 to 250 parts by weight, and the amount of the organic solvent is preferably 50 to 500 parts by weight and more preferably 50 to 250 parts by weight, to 100 parts by weight of licorice. In such a case, the ratio of the oil and fat solvent to the organic solvent (oil and fat solvent/organic solvent) is preferably 0.01 to 10 and more preferably 0.1 to 5.

The resultant oil and fat composition containing hydrophobic components of licorice can be used as the oil and fat composition of the present invention in the form of a crude extract or semipurified extract as long as it does not contain impurities inappropriate for use as pharmaceutical products or food. The resultant oil and fat composition may be subjected to purification treatment, such as decolorization and deodorization, using various adsorbents, etc., if necessary.

The oil and fat composition containing hydrophobic components of licorice according to the present invention contains flavonoid components, which have medicinal properties, for example, glycycoumarin, glycyrol, glycyrin, liquiritigenin, glicoricone, glabridin, glabrene, glabrol, 3'-hydroxyl-4'-O-methylglabridin, 4'-O-methylglabridin, hyspaglabridin B, glyurallin B, licocoumarone, gancaonin I, dehydroglyasperin D, echinatin, isolicoflavonol, dehydroglyasperin C, glyasperin B, glycyrrhisoflavanone, lupiwighteone, glyasperin D, and semilicoisoflavone B. The higher contents of these components are preferable in view of the hypoglycemic action and the lipid metabolism-improving action.

The oil and fat composition of the present invention may be used alone for food to be cooked or in preparing soft capsules, etc. In addition, since the oil and fat composition of the present invention is miscible with a fat object, the physical properties of the composition may be adjusted by adding another edible oil and fat depending on the purpose. In such a case, the type and the amount of the other edible oil and fat used are determined in consideration of various conditions, such as the physical properties required for the product and the service temperature range. By adjusting the type and the amount of the other edible oil and fat to be added, properties, such as consistency and melting point, can be controlled.

As the other edible oils and fats, the same animal and vegetable oils and fats as those usable in combination with the fat-soluble polyhydric alcohol fatty acid ester as the oil and fat solvent, which have been described above, may be used. Examples thereof include vegetable oils, such as corn oil, rapeseed oil, rapeseed oil with a high erucic acid content, soybean oil, olive oil, safflower oil, cottonseed oil, sunflower oil, rice bran oil, palm oil, and palm kernel oil; animal oils, such as fish oil, beef tallow, lard, milk fat, and yolk oil; oils and fats produced by fractionation, hydrogenation, transesterification, or the like using these oils as starting materials; and mixtures of these oils and fats.

The edible oil and fat compositions thus obtained can be used as liquid oils and fats, such as frying oils; and as oils and fats having plasticity, such as margarine and shortening. The edible oil and fat compositions can also be used for water-in-oil emulsions and oil-in-water emulsions.

Examples of the oil and fat-containing food containing the oil and fat composition of the present invention include confectionery, such as chewing gum, chocolates, candies, jelly, mousses, biscuits, and crackers; frozen desserts, such as ice cream and sherbet; beverages, such as tea, soft drinks, nutrition supplement drinks, and beauty drinks; noodles and pasta, such as Japanese wheat noodles, Chinese noodles, spaghetti, and instant noodles; fish paste products, such as kamaboko (fish cake), chikuwa (tubular fish cake), and hanpen (soft white fish cake); flavoring materials, such as dressings, mayonnaise, and sauce; and other foods, such as bread, ham, soup, various types of retort pouch food, and various types of frozen food. The oil and fat-containing food can also be used for pet food, feedstuff, etc.

Furthermore, for the purpose of enrichment, various vitamins such as A, D, and E may be incorporated into or used in combination with the oil and fat-containing food. As taste enhancers, various flavors and dairy substances, such as whole milk powder, skim milk powder, fermented milk, all kinds of salts, and milk fat, may also be incorporated into or used in combination with the oil and fat-containing food.

Besides the additives described above, it is possible to use all the additives, such as antioxidants and coloring agents, that are used for usual water-in-oil emulsions and oil-in-water emulsions.

The oil and fat-containing food can be produced incorporating the oil and fat composition of the present invention using a conventional method depending on the type, the form, and the like.

BEST MODE FOR CARRYING OUT THE INVENTION

While the present invention will be described in detail based on the examples below, it is to be understood that the invention is not limited thereto. In the following description, the terms "parts" and "%" mean "parts by weight" and "% by weight", respectively.

EXAMPLE 1

Licorice powder (kaneka San Spice Co., Ltd.) in an amount of 30 parts was mixed with 100 parts of a glycerol fatty acid ester (Sunfat GDO-D, Taiyo Kagaku Co., Ltd.; HLB=3.0; fatty acid moiety: mainly composed of oleic acid; monoglycerides 4% and diglycerides 96%), and the mixture was stirred under reduced pressure at 60° C. for 3 hours. Insolubles were then removed by filtration under reduced pressure. Oil and fat Composition 1 was thereby obtained.

EXAMPLE 2

Oil and fat Composition 2 was obtained with the same mixing ratio and operation as those in Example 1 except that a glycerol fatty acid ester (Poem Z-500, Riken Vitamin Co., Ltd.; HLB=3.1; fatty acid moiety: mainly composed of oleic acid and linoleic acid; monoglycerides 40%, diglycerides 45%, and triglycerides 15%) was used.

EXAMPLE 3

Oil and fat Composition 3 was obtained with the same mixing ratio and operation as those in Example 1 except that a medium-chain triglyceride (Actor M2, Riken Vitamin Co., Ltd.; HLB=0; fatty acid moiety: mainly composed of caprylic acid) was used.

EXAMPLE 4

Licorice powder (Kaneka San Spice Co., Ltd.) in an amount of 30 parts was mixed with 50 parts of a medium-chain triglyceride (Actor M2, Riken Vitamin Co., Ltd.; HLB=0; fatty acid moiety: mainly composed of caprylic acid) and 50 parts of 95% ethanol, and the mixture was stirred at 40° C. for 1 hour. Insolubles were then removed by filtration under reduced pressure, and ethanol was removed by distillation. Oil and fat Composition 4 was thereby obtained.

EXAMPLE 5

Licorice powder (Kaneka San Spice Co., Ltd.) in an amount of 30 parts was mixed with 150 parts of 95% ethanol, and the mixture was stirred at room temperature for 3 hours. After insolubles were removed by filtration under reduced pressure, 20 parts of a medium-chain triglyceride (Actor M2, Riken Vitamin Co., Ltd.; HLB=0; fatty acid moiety: mainly composed of caprylic acid) was mixed therewith. Stirring was performed at 40° C. for 1 hour, and then ethanol was removed by distillation. Oil and fat Composition 5 was thereby obtained.

EXAMPLE 6

Licorice powder (Kaneka San Spice Co., Ltd.) in an amount of 30 parts was mixed with 150 parts of 95% ethanol, and the mixture was stirred at room temperature for 3 hours. Insolubles were then removed by filtration under reduced pressure. A mixture of 18 parts of rapeseed oil (Kaneka Corporation) and 2 parts of a polyglycerol condensed ricinoleic acid ester (SY Glyster CRS-75, Sakamoto Yakuhin Kogyo Co., Ltd.; fatty acid moiety: ricinoleic acid) was added thereto, and the mixture was stirred at 40° C. for 1 hour. Ethanol was then removed by distillation. Oil and fat Composition 6 was thereby obtained.

COMPARATIVE EXAMPLE 1

Licorice powder (Kaneka San Spice Co., Ltd.) in an amount of 30 parts was mixed with 150 parts of 95% ethanol, and the mixture was stirred at room temperature for 3 hours. Insolubles were removed by filtration under reduced pressure, and ethanol was removed by distillation to yield 1.5 parts of a licorice extract. A glycerol fatty acid ester (Sunfat GDO-D, Taiyo Kagaku Co., Ltd.; HLB=3.0; fatty acid moiety: mainly composed of oleic acid) in an amount of 100 parts was added to the licorice extract, and the extract was dissolved by stirring at 40° C. for 1 hour. Oil and fat Composition 7 containing hydrophobic components of licorice was thereby obtained.

This process requires large amounts of the organic solvent and the oil and fat solvent in order to extract the hydrophobic components from licorice and to dissolve the extract. Consequently, the oil and fat composition containing the hydrophobic components of licorice was not produced inexpensively and did not have excellent handling properties.

COMPARATIVE EXAMPLE 2

A medium-chain triglyceride (Actor M2, Riken Vitamin Co., Ltd.; HLB=0; fatty acid moiety: mainly composed of caprylic acid) in an amount of 20 parts was mixed with 1.5 parts of a licorice extract obtained as in Comparative Example 1. Although the licorice extract was attempted to be dissolved in the medium-chain triglyceride by stirring at 40° C. for 10 hours, the extract was not completely dissolved. As a result, filtration was performed under reduced pressure to obtain Oil and fat Composition 8 containing hydrophobic components of licorice. The amount of the undissolved licorice extract was about 30% by weight.

In this process, the same amount of the oil and fat solvent was used and stirring was performed at the same temperature as that in Example 5. Even with a longer stirring time, the licorice extract could not be completely dissolved. Consequently, the oil and fat composition containing the hydrophobic components of licorice was not produced inexpensively and did not have excellent handling properties.

EXPERIMENTAL EXAMPLE 1

<Polyphenol Analysis>

With respect to Oil and fat Compositions 1 to 8 obtained in Examples 1 to 6 and Comparative Examples 1 and 2 and the licorice extract obtained in Comparative Example 1, the polyphenol content (flavonoid content) was determined by the Folin-Denis method using (+)-catechin as standard. The analytical results are shown in Table 1 below.

Herein, the observed value of the polyphenol content is determined by the method described above. The theoretical value of the polyphenol content is calculated, on the basis of the polyphenol content in the licorice extract obtained in Comparative Example 1, according to the following equation:

$$\text{Polyphenol content (\%)} = \frac{\text{Licorice extract (g)} \times \text{Polyphenol content in licorice extract (\%)}}{\text{Licorice extract (g)} + \text{Oil and fat solvent (g)}}$$

$$= \frac{1.5 \text{ (g)} \times 28.012 \text{ (\%)}}{1.5 \text{ (g)} + \text{Oil and fat solvent (g)}}$$

As is evident from Table 1, when the polyphenol content in the licorice extract obtained in Comparative Example 1 is taken as the reference, the polyphenol content in each of Oil and fat Compositions 1 to 6 of the present invention exceeds 96%. It is thus confirmed that the oil and fat compositions obtained by the production processes of the present invention are highly useful.

TABLE 1

| | Observed polyphenol content (wt. %) | Licorice/Oil and fat (weight ratio) | Theoretical polyphenol content (wt. %) | Extraction rate (%) |
|---|---|---|---|---|
| Oil and fat composition 1 according to Example 1 | 0.399 | 0.3 | 0.414 | 96.4 |
| Oil and fat composition 2 according to Example 2 | 0.403 | 0.3 | 0.414 | 97.3 |
| Oil and fat composition 3 according to Example 3 | 0.405 | 0.3 | 0.414 | 97.8 |
| Oil and fat composition 4 according to Example 4 | 0.803 | 0.6 | 0.816 | 98.4 |
| Oil and fat composition 5 according to Example 5 | 1.945 | 1.5 | 1.954 | 99.5 |
| Oil and fat composition 6 according to Example 6 | 1.897 | 1.5 | 1.954 | 97.1 |
| Oil and fat composition 7 according to Comparative Example 1 | 0.414 | 0.3 | 0.414 | 100.0 |
| Oil and fat composition 8 according to Comparative Example 2 | 1.331 | 1.5 | 1.954 | 68.1 |
| Licorice extract according to Comparative Example 1 | 28.012 | — | — | — |

EXPERIMENTAL EXAMPLE 2

<Preparation of Samples for HPLC Analysis>

Acetone (90 µl) was added to 10 µl of each of Oil and fat Compositions 1 to 6 obtained in Examples 1 to 6 to prepare a solution. The resulting solutions were diluted 10 times with methanol for HPLC to prepare samples for analysis. A methanol solution (1 mg/ml) of the licorice extract obtained in Comparative Example 1 was prepared as a sample for analysis.

<HPLC Conditions>

Column: Nacalai Tesque, COSMOSIL 5C18ARII, 4.6× 250 mm

Column temperature: 40° C.

Mobile phase: A=water:acetic acid (55:5=v/v)

B=acetonitrile

Gradient: The percentage of B to the mobile phase A was maintained at 20% for 10 minutes from the start of analysis, increased at a constant rate so that the percentage reached 70% after 60 minutes, and maintained at 70% from 60 minutes to 70 minutes.

Flow rate: 1 ml/minute

Wavelength: 254 nm

Injected sample amount: 20 µl

<Analytical Results>

As a result of comparison of the individual HPLC analytical charts, it is found that the peaks in each of Oil and fat Compositions 1 to 6 of the present invention are exactly identical to the peaks of the hydrophobic components of licorice obtained by ethanol extraction in Comparative Example 1. The concentrations of the hydrophobic components of licorice estimated based on the peak area are close to the theoretical values. It is thus confirmed that the oil and fat compositions obtained by the production processes of the present invention are highly useful.

Example 7

<Preparation of Oil Phase>

Oil and fat Composition 1 (15 parts) obtained in Example 1 and rapeseed oil (15 parts) were mixed with each other under heating at 70° C., and lecithin (0.1 parts) and a polyglycerol fatty acid ester (0.1 parts) were dissolved therein in that order to prepare an oil phase.

<Preparation of Aqueous Phase>

An albuminous protein (1 part) and skim milk (60 parts) were heated to 50° C., and a sucrose fatty acid ester (0.1 parts) and granulated sugar (10 parts) were added thereto to prepare an aqueous phase.

<Preparation of Oil-in-Water Emulsion>

The aqueous phase and the oil phase prepared as described above were preliminarily emulsified and then sterilized at 145° C. for 4 seconds with a UHT sterilizer. Subsequently, after vacuum cooling, the mixture was homogenized at a pressure of 90 kg/cm$^2$ with a homogenizer and then plate-cooled to 10° C. to prepare a cream.

<Preparation of Mousse>

Granulated sugar (13 parts), isomerized sugar (10 parts), and a gelling agent (1 part) were dissolved in water (51 parts) under heating at 90° C., and cream (15 parts) and yogurt (10 parts) were mixed therewith. The pH was adjusted to 4.0 with citric acid. The resulting mixture was charged into a cup, sterilized at 85° C. for 20 minutes, and cooled to obtain a mousse.

EXAMPLE 8

<Preparation of Oil Phase>

Oil and fat Composition 3 (70 parts) obtained in Example 3, hardened corn oil (melting point 40° C., 30 parts), and lecithin (0.5 parts) were mixed with each other under heating at 60° C. to prepare an oil phase.

<Production of Margarine>

Water (16.5%) was added to the resulting oil phase (83.5%) while stirring to perform emulsification for 20 minutes. The mixture was kneaded under cooling with a combinator to produce margarine.

EXAMPLE 9

Using a mixture of soft flour (100 parts), the margarine produced in Example 8 (35 parts), white superior soft sugar (40 parts), whole egg (5 parts), salt (0.5 parts), and water (18 parts), biscuits were produced according to a conventional method.

INDUSTRIAL APPLICABILITY

In accordance with the present invention, it is possible to produce an oil and fat composition containing hydrophobic components of licorice inexpensively and with excellent stability and handling properties. Furthermore, food and drink, such as health food and food with health claims (food for specified health uses and food with nutrient function claims), pharmaceutical products, pet food, feedstuff, etc. which include the oil and fat composition of the present invention have a hypoglycemic action and a lipid metabolism-improving action, and thus are significantly advantageous in industrial applications.

The invention claimed is:

1. A process for producing an oil and fat composition containing hydrophobic components of licorice, comprising mixing licorice with an oil and fat solvent containing 10% by weight or more of a fat-soluble polyhydric alcohol fatty acid ester in the oil and fat solvent.

2. The process for producing an oil and fat composition containing hydrophobic components of licorice according to claim 1, wherein the licorice is mixed with the oil and fat solvent used together with at least one organic solvent selected from the group consisting of ethanol, acetone, and ethyl acetate.

3. The process for producing the oil and fat composition containing hydrophobic components of licorice according to claim 2, wherein at least one organic solvent selected from the group consisting of ethanol, acetone, and ethyl acetate is mixed with licorice, and then the oil and fat solvent containing 10% by weight or more of the fat-soluble polyhydric alcohol fatty acid ester is mixed therewith.

4. The process for producing the oil and fat composition containing hydrophobic components of licorice according to claim 1, wherein the oil and fat solvent contains only the fat-soluble polyhydric alcohol fatty acid ester.

5. The process for producing the oil and fat composition containing hydrophobic components of licorice according to claim 1, wherein the fat-soluble polyhydric alcohol fatty acid ester is a glycerol fatty acid ester.

6. The process for producing the oil and fat composition containing hydrophobic components of licorice according to claim 5, wherein the glycerol fatty acid ester is a monoglyceride and/or a diglyceride.

7. The process for producing the oil and fat composition containing hydrophobic components of licorice according to claim 5, wherein the glycerol fatty acid ester is a medium-chain triglyceride.

8. The process for producing the oil and fat composition containing hydrophobic components of licorice according to claim 5, wherein the glycerol fatty acid ester is a polyglycerol fatty acid ester.

9. The process for producing the oil and fat composition containing hydrophobic components of licorice according to claim 8, wherein the polyglycerol fatty acid ester is a polyglycerol condensed ricinoleic acid ester.

10. An oil and fat composition containing hydrophobic components of licorice produced by the process according to claim 6.

11. An oil and fat-containing food comprising the oil and fat composition containing hydrophobic components of licorice according to claim 10.

12. An oil and fat composition containing hydrophobic components of licorice produced by the process according to claim 7.

13. An oil and fat-containing food comprising the oil and fat composition containing hydrophobic components of licorice according to claim 12.

14. A process for producing an oil and fat composition containing hydrophobic components of licorice, comprising the steps of:

providing an oil and fat solvent containing 10% or more by weight of a fat-soluble polyhydric alcohol fatty acid ester;

providing licorice in a form other than as an extract obtained by extraction with a common organic solvent;

mixing the licorice in said form with said oil and fat solvent containing 10% or more by weight of a fat-soluble polyhydric alcohol fatty acid ester; and obtaining an oil and fat composition containing hydrophobic components of licorice by removing insolubles from the mixture.

15. The process of claim 14 further including the steps of:

mixing the licorice in said form with at least one organic solvent selected form the group consisting of ethanol, acetone, and ethyl acetate and, then;

mixing the oil and fat solvent containing 10% more by weight of the fat-soluble polyhydric alcohol fatty acid ester with the licorice and organic solvent mixture.

* * * * *